United States Patent [19]

Poler

[11] 4,301,802
[45] Nov. 24, 1981

[54] CAUTERIZING TOOL FOR OPHTHALMOLOGICAL SURGERY

[76] Inventor: Stanley Poler, 78 E. Second St., New York, N.Y. 10003

[21] Appl. No.: 131,198

[22] Filed: Mar. 17, 1980

[51] Int. Cl.³ ............................................. A61B 17/36
[52] U.S. Cl. ............................ 128/303.14; 128/295.1
[58] Field of Search .................... 128/305.13–305.18, 128/275.1, 278, 800

[56] References Cited

U.S. PATENT DOCUMENTS

| | | | |
|---|---|---|---|
| 2,102,270 | 12/1937 | Hyams | 128/303.17 |
| 2,275,167 | 3/1942 | Bieman | 128/303.17 |
| 3,078,850 | 2/1963 | Schein et al. | 128/303.13 |
| 3,680,544 | 8/1972 | Shinnick et al. | 128/348 X |
| 3,682,162 | 8/1972 | Colyer | 128/303.18 X |
| 3,884,237 | 5/1975 | O'Malley et al. | 128/303.14 |
| 4,103,688 | 8/1978 | Edwards | 128/303.17 |

FOREIGN PATENT DOCUMENTS 57862 9/1953 France ............................ 128/303.14

OTHER PUBLICATIONS

Peyman et al., "Experimental Intraoculer Coagulation", Opthalmic Surgery, Jan.–Feb. 1972, vol. 3, No. 1, pp. 32–37.

*Primary Examiner*—Lee S. Cohen
*Attorney, Agent, or Firm*—Hopgood, Calimafde, Kalil, Blaustein & Judlowe

[57] ABSTRACT

The invention contemplates a cauterizing tool in which the localized working surface of a cauterizing electrode is at an offset end of an elongate tubular body which may be of hypodermic-needle proportions and which is adapted for syringe connection to enable manipulation and irrigation of the region of cauterizing surgery, without need to remove the cauterizing tool. In ophthalmological surgery, the tool enables trans-iris placement and manipulation of the electrode region for clean circular cutting and irrigation of the anterior wall of the lens capsule, as a preliminary to removal of cataracted lens material from within the capsule.

8 Claims, 5 Drawing Figures

TO CAUTERY POWER SUPPLY

CAUTERIZING TOOL FOR OPHTHALMOLOGICAL SURGERY

BACKGROUND OF THE INVENTION

The invention relates to a combined tool for enabling the surgeon to bring both electrical cauterizing and irrigation functions to a relatively small region of surgical operation, as when surgically entering a lens capsule in the course of a cataract-removal operation.

In such cataract-removal surgery as to which I am informed, it has been the practice to employ a sharp instrument to locally tear the anterior wall of a natural-lens capsule, in order to gain access for insertion of a second instrument to remove cataracted lens material. The sharp instrument has been a conventional hypodermic needle with a conventionally sloping truncated tip, and the instrument has been fashioned by the surgeon himself, by bending the tapered end of the tip into a right-angle bend, thus forming a pointed hook, for scraping, piercing and locally tearing the anterior wall of the capsule. Once sufficient access is thus gained, the second tool is inserted, to bring circularly cut straight ends of concentric tubes into the region of cataracted lens material; one of the tubes is supplied with a flow of irrigating fluid while the other is under reduced evacuation pressures to remove both the irrigation fluid and the severed lens material entrained therewith. In some cases, the second tool includes an ultrasonic element to emulsify the lens material for easier extraction via the evacuating return flow of the irrigation.

Whatever the technique, to my knowledge, there is no means other than cutting or tearing, for removal of the anterior wall of the lens capsule. And this fact has presented difficulties to the surgeon who opts to install an intraocular lens within remaining confines of the lens capsule, in accordance with either of the operative procedures described in my copending patent application Ser. No. 127,450, filed Mar. 5, 1980. For such procedures, it is highly desirable to achieve relative uniformity, circumferential continuity and tissue integrity at the region of the capsule rim through which the implanted lens (including associated haptic structure) is operatively inserted and upon which reliance is placed for stabilized lens retention via the haptic structure.

BRIEF STATEMENT OF THE INVENTION

It is an object of the invention to provide improved surgical instrumentation of the character indicated.

A specific object is to provide an improved tool for operatively removing the anterior wall of the lens capsule of a cataracted natural lens.

It is also a specific object to achieve the above objects with a tool which can be operated without tearing body tissue and which, additionally, will enable the cut rim of a circular opening in the anterior wall of the lens capsule to be surgically fashioned for reliable and effective engagement with haptic structure which provides positioning support of an intraocular lens, implanted in the lens capsule after removal of cataracted lens material.

Another specific object is to provide means in such a tool for selective application of cauterizing functions and irrigation functions via such a tool, without need for removing the tool.

A general object is to meet the above objects with a tool of basic simplicity and of such relatively low cost as to enable its use as a disposable attachment to a reusable holding and manipulating device.

The foregoing and other objects and features of the invention are realized in a cauterizing tool in which the locally exposed working surface of a cauterizing electrode is at an offset end of an elongate tubular body of hypodermic-needle proportions and dimensions and which is adapted for removable syringe connection to enable manipulation and irrigation at the region of cauterizing surgery. The tool enables trans-iris placement and manipulation of the electrode region for clean tear-free circular cutting and irrigation of the anterior wall of the lens capsule, all without need to remove the cauterizing tool, and producing hitherto unachieved uniformity, circumferential continuity and tissue integrity at the resulting capsule rim via which the lens implant is to be made.

DETAILED DESCRIPTION

Preferred forms of the invention will be described in detail in conjunction with the accompanying drawings, in which.

Figure 1:
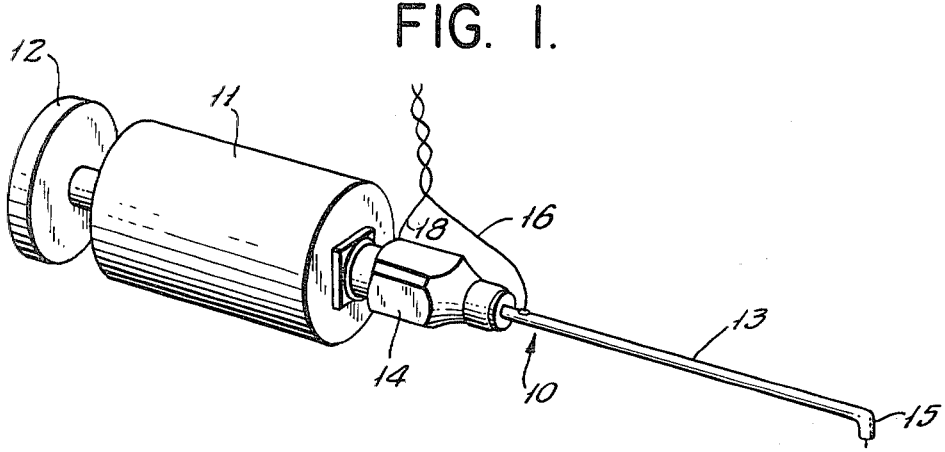
FIG. 1 is a perspective view of a tool attachment of the invention, in assembled relation to a syringe.
Figure 2:
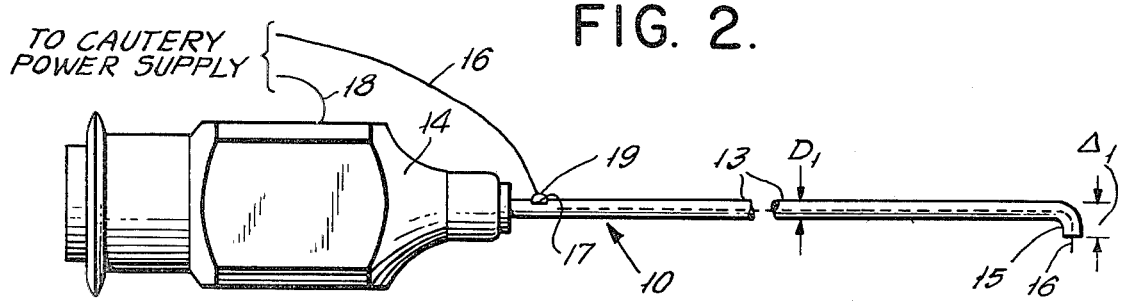
FIG. 2 is an enlarged side-elevation view of the tool attachment of FIG. 1.
Figure 3:
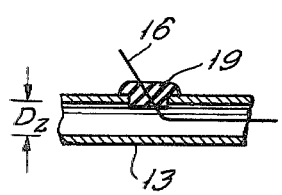
FIGS. 3 and 4 are enlarged fragmentary sectional views of different parts of the tool attachment of FIGS. 1 and 2.

Referring to FIGS. 1 to 4, the invention is shown in application to a tool attachment 10, removably attachable to a syringe body 11, having a plunger with an external actuator 12 for selective delivery of irrigating fluid, such as a saline solution, to the tool attachment 10. As shown, the tool attachment 10 is constructed by modification of a conventional hypodermic-needle sub-assembly, having an elongate slender tubular body 13, with a syringe-attachment fitting 14 at its supply end, and with a substantially right-angle bend at its discharge end 15. For the opthalmological-surgery application in connection with which the invention finds present use, a so-called 25-gauge hypodermic-needle attachment is a satisfactory starting point, in which case the outside diameter $D_1$ of body 13 is 0.040 inch.

At the bent or discharge end 15, the maximum transverse span $A_1$ is short, being at least no greater than substantially twice the diameter $D_1$ but being preferably small enough, e.g., 0.060 inch, for ready insertion through and manipulation within the pupil opening of the iris, in the course of gaining surgical access to the anterior wall of the lens capsule; the net radial offset $A_2$ of the discharge end 15 is thus illustratively 0.020 inch. Electric-cable means 16 is supported by and within the bore of body 13, being brought through a side port 17 for external connection to a cautery power supply, and projecting to an extent $A_3$ beyond the discharge end 15, where to an extent $A_4$ (which is preferably less than $A_3$) the insulation of cable means 15 is stripped to expose one or more cauterizing-electrode surfaces. The cable means 16 may comprise two insulated conductors providing independent spaced exposed electrode surfaces in the region $A_4$; but in its simpler and preferred form, cable means 16 is a single Teflon-coated platinum wire, having an external diameter of 0.006 inch (measured over the coat) and thus presenting negligible section-area reduction within the bore of body 13. The material of the attachment 10 is electrically conductive, and therefore a return power-supply lead connection 18 to fitting 14 enables development of cauterizing voltage between the electrode surface (exposed at $\Delta_4$) and the adjacent rim of the discharge end 15. A sealing bead 19, as of epoxy material, closes the side port 17 and provides fixed retention of cable means 16 at entry into body 13.

Figure 4:
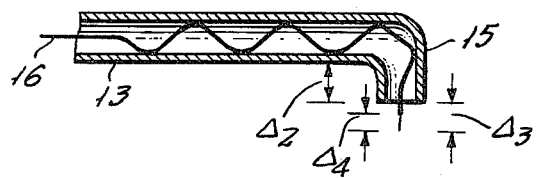

FIG. 4 shows that for stabilized central positioning of the projecting electrode-surface end of cable 16, a plurality of sinusoidal or zig-zag bends are preset in the electrode end of the cable, prior to its being drawn into final position at and near the discharge end. The unstressed amplitude of zig-zag or sinusoidal excursion should slightly exceed the bore diameter of body 13, so that when drawn into the fully assembled position shown in FIG. 4, the electrode end derives stabilized positioning from a plurality of longitudinally opposed contacts with the bore of body 13. Sufficient cable 16 projects beyond end 15 to enable a suitable forming tool, such as pliers, to create a permanent and sufficiently centered orientation at and throughout the projecting region $\Delta_3$.

In a cataract-removal surgery, the described tool finds use after an upper arc of the cornea has been cut just forward of the scleral ridge, thus providing an incision slot for lateral entry of body 13, and enabling trans-iris manipulation of the bent end 15 and of the cauterizing electrode region of cable 16 into a substantially normal orientation with respect to the anterior wall of the lens capsule. In a first arcuate surgical pass wherein body 13 is near one end of the corneal incision, and with cauterizing voltage applied, the anterior wall of the lens capsule may be cut to approximately a first semicircular locus on the remote side of the optical axis of the eye, and in a succeeding such pass wherein body 13 is near a diametrically opposite portion of the corneal incision, the capsule wall may be similarly cut along a second semicircular locus which, with the first such locus, completes a circular cauterized cut of the anterior wall, to enable removal of the cut central area. In the course of making these cauterizing cuts, e.g., in intermittent alternation with increments of the respective semicircular cuts, the syringe may be actuated at 12, to freshly irrigate each increment of cut. The result is a circumferentially continuous fully cauterized rim, illustratively of 6 to 8-mm diameter and thus capacitated for ultimate implantation of a selected one of the lens assemblies of my said copending application.

Figure 5:
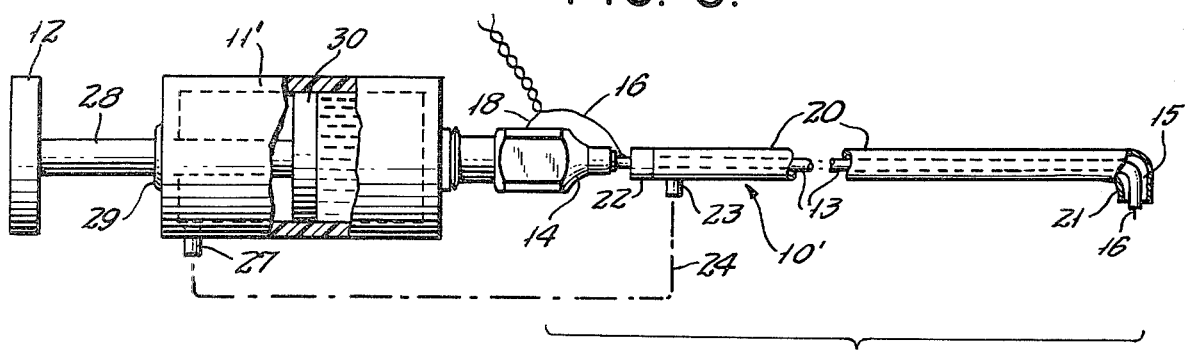
FIG. 5 is a simplified side-elevation view of a modified tool of the invention, certain parts being broken-away and in longitudinal section.

In the modification of FIG. 5, the tool attachment 10' may be as described at 10 in connection with FIGS. 1 to 4, except that an additional or outer tubular member 20 surrounds body 13 with sufficient clearance to establish a return-flow passage for removal of irrigation fluid from the area of surgery. Thus, member 20 has a bent end 21 surrounding the discharge end 15 of body 13, and at its end near fitting 14, the tubular member 20 is closed and mounted to body 13, at 22. Adjacent the mounting 22, a side-port fitting 23 is poised to accept resilient slip-fit of a flexible elastomeric evacuation hose 24 for external connection to suitable evacuating means.

In the form shown, slightly reduced pressure for evacuation purposes is derived from plunger action at the tail end of the cylinder 11' of the syringe to which fitting 14 is removably connected. The tail end of cylinder 11' has a suction-port fitting 27 over which the other end of hose 24 is removably securable; the piston rod 28 for cylinder 11' has elastomerically sealed passage at 29 into the tail end, and the associated piston 30 has similarly sealed fit to the bore of cylinder 25. Depression of the single actuator button 12 thus provides positive discharge of irrigation fluid from the head end of cylinder 11' and at least a transient reduced-pressure development at the tail end of the cylinder.

Cauterizing operation of the FIG. 5 embodiment is as described for FIGS. 1 to 4. However, for irrigation purposes, inward displacement of actuator 12 not only discharges syringe fluid at the zone of surgery but also momentarily creates a reduced pressure for extraction of fluid from the zone of surgery, via the space between the bent ends 15-21. Each incremental depression of actuator 12 can be used to extract more irrigating fluid as desired; and, having first made a suitable cauterizing puncture in the central region of the wall segment to be removed, a reduced pressure in the tail end of cylinder 11' may be an aid to manipulated extraction of the cut circular segment of the anterior wall of the lens capsule, as will be understood.

The described embodiments of the invention will be seen to achieve all stated objects. No torn tissues are involved in use of the tool, and a superior cut is achieved, well-adapting the lens capsule to receive and support its implanted lens. Although the attachment tool of the invention is of fully autoclavable materials and may thus be reused if desired, the article is of manifestly lowcost construction and may thus be discarded upon each use, relying upon an inventory of similar sterilized tool attachments, one for each surgical use.

While the invention has been described in detail for the preferred forms shown, it will be understood that modifications may be made without departure from the scope of the invention.

What is claimed is:

1. As an article of manufacture, a cauterizing tool comprising a tubular hypodermic-needle shaft having an elongate body with a syringe-adapter fitting at an upstream supply end and a substantially right-angle bend at a downstream discharge end, the radial offset at said bend being a small fraction of the elongate length of said shaft, and electrically conductive cable means for electrical cauterizing supply to said discharge end, said cable means being of cross-sectional area less than that of the bore of said shaft and extending within and for the preponderance of the length of said shaft, said cable means projecting through and beyond the discharge end of said shaft and having an externally exposed conductive working-electrode surface at said discharge end, whereby when fitted to a syringe having a supply of suitable irrigation fluid, and when said cable means is connected for excitation with a supply of cauterizing voltage, a region of cauterizing surgery may be irrigated without need for removal of the working-electrode surface from the region of surgical operation, said cable means being characterized by preformed zig-zag bends within said shaft near said discharge end, the zig-zag offsets in unstressed condition being greater than the bore diameter of said shaft, whereby said cable means is compliantly loaded in stabilizing contact with the bore of said shaft near said electrode surface for stabilized positioning support of said working-electrode surface with respect to said discharge end.

2. The article of claim 1, in which said discharge end projects radially outside the geometrical projection of said elongate body to an extent which is in the order of magnitude of the diameter of said body.

3. The article of claim 2, in which said extent is less than the diameter of said body projection.

4. The article of claim 1, in which said cable means comprises a single conductor having an insulating coat which extends continuously to said working-electrode surface, said shaft being electrically conductive and adapted at or near its supply end for electrical circuit connection to the supply of cauterizing voltage.

5. The article of claim 1, in which said body has a lateral aperture near its supply end, said cable means passing through said aperture for cauterizing voltage-supply connection, and fluid-tight means sealing said cable means at aperture passage.

6. The article of claim 4, in which said cable means is a Teflon-coated platinum wire.

7. As an article of manufacture, a cauterizing tool comprising a tubular hypodermic-needle shaft having an elongate body with a syringe-adapter fitting at an upstream supply end and a substantially right-angle bend at a downstream discharge end, the radial offset at said bend being a small fraction of the elongate length of said shaft, electrically conductive cable means for electrical cauterizing supply to said discharge end, said cable means being of cross-sectional area less than that of the bore of said shaft and extending within and for the preponderance of the length of said shaft, said cable means projecting through and beyond the discharge end of said shaft and having an externally exposed conductive working-electrode surface at said discharge end, whereby when fitted to a syringe having a supply of suitable irrigation fluid, and when said cable means is connected for excitation with a supply of cauterizing voltage, a region of cauterizing surgery may be irrigated without need for removal of the working-electrode surface from the region of surgical operation, a further elongate tubular member enclosing said shaft with clearance to define an evacuation passage, said tubular member being open adjacent the discharge end of said shaft and closed at the supply end of said shaft, said tubular member having evacuation-port means near said closed end.

8. The article of claim 7, in which syringe means includes a cylinder with a head end connected to said fitting for supply of irrigation fluid to said discharge end, said cylinder having a tail end having sealed evacuation-fluid connection to said evacuation-port means.

* * * * *